US009072433B2

(12) United States Patent
Chen et al.

(10) Patent No.: US 9,072,433 B2
(45) Date of Patent: Jul. 7, 2015

(54) METHOD AND APPARATUS FOR NONINVASIVE BLOOD PRESSURE MEASUREMENT USING PULSE OXIMETRY

(75) Inventors: Bo Chen, Louisville, CO (US); Youzhi Li, Longmont, CO (US); Daniel Lisogurski, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 766 days.

(21) Appl. No.: 13/030,385

(22) Filed: Feb. 18, 2011

(65) Prior Publication Data

US 2012/0215082 A1 Aug. 23, 2012

(51) Int. Cl.
*A61B 5/02* (2006.01)
*A61B 5/022* (2006.01)
*A61B 5/024* (2006.01)
*A61B 5/021* (2006.01)

(52) U.S. Cl.
CPC ............ *A61B 5/022* (2013.01); *A61B 5/02422* (2013.01); *A61B 5/02108* (2013.01)

(58) Field of Classification Search
CPC . A61B 5/02422; A61B 5/022; A61B 5/02108
See application file for complete search history.

(56) References Cited

U.S. PATENT DOCUMENTS 4,776,339 A 10/1988 Schreiber
5,152,296 A 10/1992 Simons
5,253,645 A 10/1993 Friedman et al.
5,309,908 A 5/1994 Friedman et al.
5,343,869 A 9/1994 Pross et al.
5,379,774 A * 1/1995 Nishimura et al. ........... 600/479
5,515,847 A 5/1996 Braig et al.
5,517,988 A 5/1996 Gerhard
5,531,776 A 7/1996 Ward et al.
5,766,127 A 6/1998 Pologe et al.
5,891,025 A 4/1999 Buschmann et al.
5,983,129 A * 11/1999 Cowan et al. ................ 600/544
6,035,223 A 3/2000 Baker, Jr.
6,129,675 A 10/2000 Jay
6,135,966 A 10/2000 Ko
6,322,515 B1 11/2001 Goor et al.
6,325,761 B1 12/2001 Jay
6,405,075 B1 6/2002 Levin (Continued)

FOREIGN PATENT DOCUMENTS

WO WO9817174 A1 4/1998
WO WO0074551 12/2000
WO WO0187143 11/2001

OTHER PUBLICATIONS

Kyriacou et al., "*Arterial Blood Oxygen Saturation During Blood Pressure Cuff-Induced Hypoperfusion*", 3d Int'l Conference on Optical and Laser Diagnostics, Journal of Physics: Conference Series 85 (2007) 012026, pp. 1-8.

(Continued)

*Primary Examiner* — Michael D'Angelo
*Assistant Examiner* — Christian Jang
(74) *Attorney, Agent, or Firm* — Fletcher Yoder PC

(57) ABSTRACT

Embodiments of the present disclosure relate to a system and method for determining a physiologic parameter of a patient. Specifically, embodiments provided herein include blood pressure cuffs that are adapted to be used in conjunction with a photoplethysmography sensor. The cuff as provided may be configured to be placed over the sensor and/or aligned in a specific manner relative to the sensor. Alternatively, the cuffs may include integral optical components.

19 Claims, 6 Drawing Sheets

196
18
14
198
199
SENSOR
188
20
194
192
180
190

(56) References Cited

U.S. PATENT DOCUMENTS 6,434,408 B1 8/2002 Heckel
6,832,987 B2 12/2004 David et al.
6,839,582 B2 1/2005 Heckel
6,840,904 B2 1/2005 Goldberg
6,869,402 B2 3/2005 Arnold
6,879,850 B2 4/2005 Kimball
6,988,992 B2 * 1/2006 Just et al. ...................... 600/499
7,039,538 B2 5/2006 Baker, Jr.
7,044,917 B2 5/2006 Arnold
7,066,173 B2 6/2006 Banner et al.
7,090,648 B2 8/2006 Sackner et al.
7,112,175 B2 9/2006 Gopinathan et al.
7,201,734 B2 4/2007 Hickle
7,210,478 B2 5/2007 Banner et
7,238,159 B2 7/2007 Banet et al.
7,247,154 B2 7/2007 Hickle
7,249,036 B2 7/2007 Bayne
7,252,636 B2 8/2007 Brown
7,277,752 B2 10/2007 Matos
7,300,404 B1 11/2007 Kolluri et al.
7,320,030 B2 1/2008 Brown
7,341,560 B2 3/2008 Henderson et al.
7,344,503 B2 3/2008 Friedman
7,390,301 B2 6/2008 Skrabal et al.
7,390,302 B2 6/2008 Friedman et al.
7,435,222 B2 10/2008 Gopinathan et al.
7,438,687 B2 10/2008 Lewicke
7,448,996 B2 11/2008 Khanuja et al.
7,462,152 B2 12/2008 Kolluri et al.
7,474,907 B2 1/2009 Baker, Jr.
7,534,212 B2 5/2009 Baker, Jr.
2001/0051767 A1 12/2001 Williams et al.
2003/0158466 A1 8/2003 Lynn et al.
2003/0212316 A1 11/2003 Leiden et al.
2004/0260156 A1 12/2004 David et al.
2005/0192500 A1 9/2005 Caro et al.
2005/0228244 A1 10/2005 Banet
2005/0228299 A1 10/2005 Banet
2005/0245831 A1 11/2005 Banet
2005/0251405 A1 11/2005 Kreiner
2005/0261598 A1 11/2005 Banet et al.
2006/0009698 A1 1/2006 Banet et al.
2006/0042631 A1 3/2006 Martin et al.
2006/0047188 A1 3/2006 Bohan
2006/0081259 A1 4/2006 Bruggeman et al.
2006/0084878 A1 4/2006 Banet et al.
2006/0111749 A1 5/2006 Westenskow et al.
2006/0149144 A1 7/2006 Lynn et al.
2006/0155206 A1 7/2006 Lynn
2006/0155207 A1 7/2006 Lynn et al.
2006/0155589 A1 7/2006 Lane et al.
2006/0161071 A1 7/2006 Lynn et al.
2006/0189871 A1 8/2006 Al-Ali et al.
2006/0189872 A1 8/2006 Arnold
2006/0189880 A1 8/2006 Lynn et al.
2006/0195037 A1 8/2006 Wiesel
2006/0212316 A1 9/2006 Jackson
2006/0220881 A1 10/2006 Al-Ali et al.
2006/0226992 A1 10/2006 Al-Ali et al.
2006/0235324 A1 10/2006 Lynn
2006/0238358 A1 10/2006 Al-Ali et al.
2006/0241975 A1 10/2006 Brown
2006/0270952 A1 11/2006 Freeman et al.
2006/0276695 A9 12/2006 Lynn et al.
2006/0285736 A1 12/2006 Brown
2006/0287590 A1 12/2006 McEowen
2006/0293712 A1 12/2006 Kieval et al.
2007/0000494 A1 1/2007 Banner et al.
2007/0021673 A1 1/2007 Arbel et al.
2007/0027369 A1 2/2007 Pagnacco et al.
2007/0060874 A1 3/2007 Nesbitt et al.
2007/0071643 A1 3/2007 Hall et al.
2007/0093721 A1 4/2007 Lynn et al.
2007/0100213 A1 5/2007 Dossas et al.
2007/0106163 A1 5/2007 Friedman et al.
2007/0118045 A1 5/2007 Naghavi et al.
2007/0129636 A1 6/2007 Friedman et al.
2007/0129647 A1 6/2007 Lynn
2007/0142715 A1 6/2007 Banet et al.
2007/0149860 A1 6/2007 Lynn et al.
2007/0185393 A1 8/2007 Zhou et al.
2007/0191688 A1 8/2007 Lynn
2007/0191693 A1 8/2007 Peng
2007/0191697 A1 8/2007 Lynn et al.
2007/0225606 A1 9/2007 Naghavi et al.
2007/0225614 A1 9/2007 Naghavi et al.
2007/0282181 A1 12/2007 Findlay et al.
2008/0004513 A1 1/2008 Walker
2008/0004907 A1 1/2008 Bayne
2008/0021379 A1 1/2008 Hickle
2008/0045846 A1 2/2008 Friedman et al.
2008/0064965 A1 3/2008 Jay et al.
2008/0076992 A1 3/2008 Hete et al.
2008/0077026 A1 3/2008 Banet et al.
2008/0082006 A1 4/2008 Kolluri et al.
2008/0082007 A1 4/2008 Friedman
2008/0091088 A1 4/2008 Kiani
2008/0091092 A1 4/2008 Al-Ali
2008/0139889 A1 6/2008 Bagan
2008/0221417 A1 9/2008 Baker et al.
2008/0221418 A1 9/2008 Al-Ali et al.
2008/0221930 A1 9/2008 Wekell et al.
2008/0243010 A1 * 10/2008 Kulik ........................... 600/499
2008/0255433 A1 10/2008 Prough et al.
2008/0281164 A1 11/2008 Stebor et al.
2008/0281168 A1 11/2008 Gibson et al.
2009/0247852 A1 10/2009 Boyce et al.
2010/0331709 A1 * 12/2010 Matsumura et al. .......... 600/490
2012/0215082 A1 8/2012 Chen et al.
2012/0215118 A1 8/2012 Chen et al.
2013/0178750 A1 7/2013 Sheehan et al.
2013/0211267 A1 8/2013 Wang et al.

OTHER PUBLICATIONS

Tochikubo et al., "*A New Photo-Oscillometric Method Employing the Delta-Algorithm for Accurate Blood Pressure Measurement*", Journal of Hypertension (1997) 15:147-156.

Tochikubo et al., "*A New Double Cuff Sphygmotonometer for Accurate Blood Pressure Measurement*", Dept. of Public Health and Second Department of Internal Medicine, Yokohama City University School of Medicine, Yokohama, Japan (Jan. 4, 2001) pp. 353-357.

Tochikubo et al., "*Recent Advances in Blood Pressure Measurement Technology: Normalized Blood Pressure Measurement with a Double-Cuff Sphygmotonometer*", Blood Pressure Monitoring Dec. 2001, 6(6):297-301.

Tochikubo et al., "Accuracy and Applicability of the Terumo ES-H55 Double-Cuff Sphygmomanometer for Hospital Use", Device and Technology (2003) pp. 203-.

U.S. Appl. No. 13/030,353, filed Feb. 18, 2011, Bo Chen et al.

* cited by examiner

METHOD AND APPARATUS FOR NONINVASIVE BLOOD PRESSURE MEASUREMENT USING PULSE OXIMETRY

BACKGROUND

The present disclosure relates generally to medical devices, and more particularly, to devices for monitoring blood pressure of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

For example, clinicians may wish to monitor various physiological parameters of a patient, such as blood pressure. Blood pressure may be non-invasively assessed using a sphygmomanometer, which is used in conjunction with an acoustic device, e.g, a stethoscope, to measure a patient's blood pressure. During a measurement, a medical professional typically places a cuff around the patient's arm and inflates it to a pressure that exceeds the systolic blood pressure. The medical professional then incrementally reduces pressure in the cuff while listening for flowing blood with the stethoscope. The pressure value at which blood first begins to flow past the deflating cuff, indicated by a Korotkoff sound, is the systolic pressure. The minimum pressure in the cuff that restricts blood flow, as detected by the stethoscope, is the diastolic pressure. The stethoscope monitors this pressure by detecting another Korotkoff sound that reflects a disappearance in the acoustic magnitude of the periodic beats, indicating that the cuff no longer restricts blood flow (i.e., the diastolic pressure barely exceeds the cuff pressure). Blood pressure measurements taken with a sphygmomanometer may be subject to the skill of the caregiver in detecting sounds associated with peak diastolic pressure.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
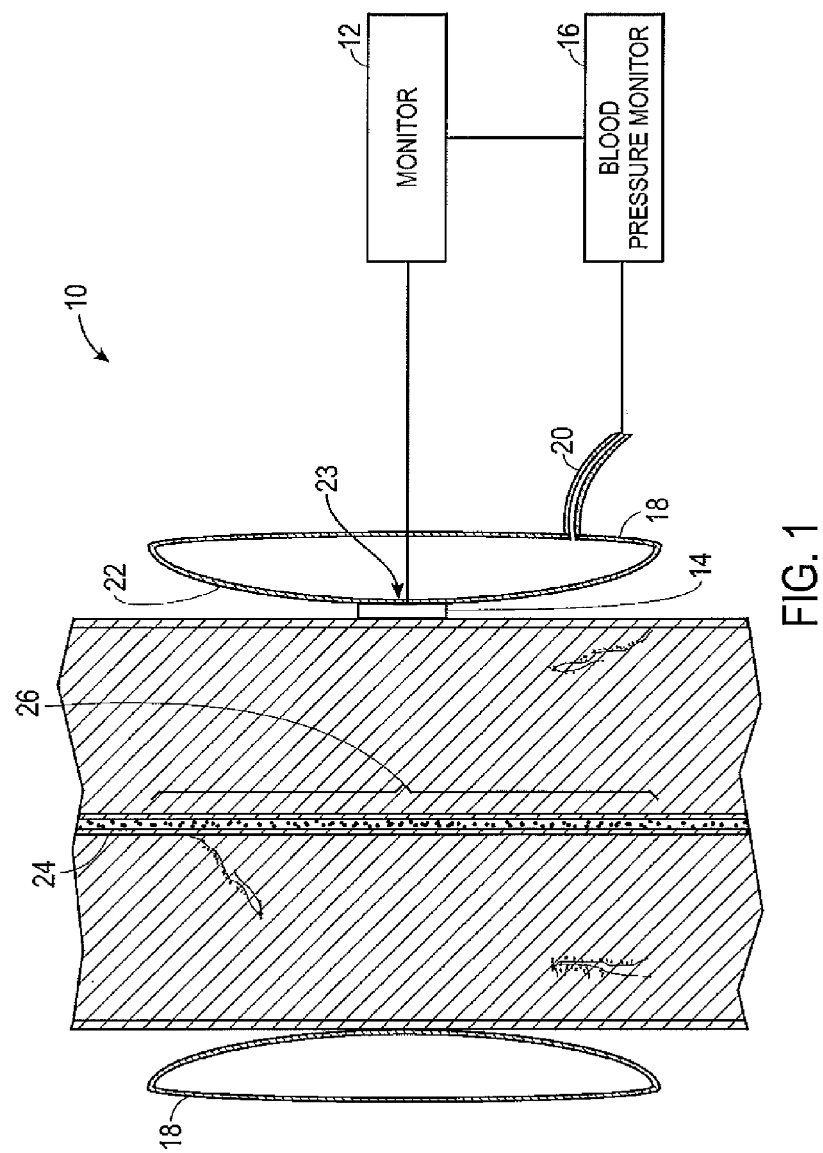
FIG. 1 is a perspective view of a medical monitoring system in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A clinician may determine a patient's blood pressure through the use of a dedicated blood pressure monitoring device and associated system. For example, a clinician may apply a blood pressure monitoring device that includes a cuff that may be inflated when applied to a patient's arm to cause a temporary disturbance in blood flow. Inflation of the cuff may slow or halt the flow of blood through the arm, while subsequent deflation of the cuff allows blood to resume normal flow. As the blood flow resumes and the arteries returns to normal pressure, a clinician may monitor the pressure in the cuff and correlate the cuff pressure to blood pressure measurements. For example, certain characteristic sounds are associated with systolic pressure and diastolic pressure points. These sounds may be monitored either manually (e.g., via a stethoscope) or automatically (e.g., via an acoustic sensor) and correlated to the pressure in the cuff at the times the sounds are detected. However, the use of monitored sounds alone may be insufficient to accurately detect the systolic and diastolic pressure. In another example, a patient's blood pressure may be determined by monitoring small changes in the pressure in the cuff that are translated from the patient's blood vessel. The changes in pressure are associated with the pulse and have a characteristic oscillation pattern. However, the pressure oscillations measurements may include relatively high levels of noise, which may reduce the accuracy of the estimated systolic and diastolic pressure.

Provided herein are devices, systems, and methods for non-invasive blood pressure monitoring that employ data from a photoplethysmography sensor (e.g., a pulse oximetry sensor) to improve the performance of a non-invasive blood pressure monitor. Combining the use of non-invasive blood pressure monitoring with information from a photoplethysmography sensor allows for more accurate detection of systolic pressure (Ps). As provided herein, a photoplethysmography sensor may be positioned inside the blood pressure cuff so that the sensor is positioned against the tissue when the cuff is applied to a patient. Inflation of the cuff to oversystolic pressure results in cessation of a detected pulse waveform at the photoplethysmography sensor, because blood flow to the tissue under the cuff is restricted. As the cuff is deflated and the blood begins to flow into the tissue, the pulse waveform resumes and is able to be detected by the photoplethysmography sensor. The cuff pressure at which the pulse waveform reemerges via sensor measurements correlates to the Ps. In this manner, photoplethysmography signals may be used to more accurately determine Ps. From the Ps as well as the mean arterial pressure, a patient's systolic and diastolic blood pressure may be determined.

In addition, provided herein are medical devices, including medical monitors and sensors, that may be used in conjunction with the non-invasive blood pressure monitoring techniques. As noted, the photoplethysmography sensor may be positioned on an interior surface of the inflatable blood pressure cuff. Depending on the configuration of the cuff, the sensor may be positioned at the area of the cuff that is roughly at a midpoint of the length of the cuff along the limb (e.g., the arm). Such positioning may provide the advantage of increased accuracy in detecting Ps by correlating the earliest appearance of the pulse waveform after tissue restriction with the appropriate intracuff pressure. Generally, the pressure sensed in the cuff corresponds most accurately to the pressure applied by center of the cuff, which may also be the point of maximum applied pressure, at approximately any circumferential location that is about halfway between the top and the bottom of the cuff. During deflation, the cuff edges may change their shape and pressure against the tissue in a less predictable manner than the portion of the cuff in the middle. By sensing the reemergence of the pulse waveform in the area of the cuff that corresponds most accurately with an intracuff pressure, the measured Ps may be associated with reduced variability. In addition, in certain embodiments, during deflation of the cuff, the pulse waveform emerges at an area of the tissue corresponding the center of the cuff. By positioning a sensor at this location, the pressure in the cuff allowing reemergence of the pulse waveform may be more accurately correlated to the Ps. In particular embodiments, the cuff may include an integral photoplethysmography sensor that is positioned appropriately. In other embodiments, the cuff may include positioning indicia or attachment devices to facilitate correct placement of the photoplethysmography sensor relative to the blood pressure cuff.

FIG. 1 is a view of a system 10 for non-invasive blood pressure monitoring of a patient. As shown, the system includes a monitor 12 that may be configured to implement the embodiments of the present disclosure. The monitor 12 is coupled to a photoplethysmography sensor 14 that includes one or more optical components configured to be applied to a patient. The monitor 12 may be used to detect a plethysmographic waveform associated with blood flow. In certain embodiments, the sensor 14 may be coupled to the monitor 12 wirelessly or via a cable. The sensor 14 may be a reflectance-type sensor. In certain embodiments, depending on the location that the cuff 18 is applied, the sensor 14 may be a transmission-type sensor. For example, if the cuff is applied about a patient's digit, the associated sensor 14 may be reflectance or transmission-type. A blood pressure monitor 16 is also included in the system 10 and may be in communication with the monitor 12. While the monitor 12 and blood pressure monitor 16 are depicted as separate devices in FIG. 1, it should be understood that, in certain embodiments, the functionality of the monitor 12 and the blood pressure monitor 16 may be combined into a single medical monitor or a multi-parameter monitor.

The blood pressure monitor 16 is coupled to an inflatable cuff 18, which is configured to be applied to a patient's limb (e.g., an arm or a leg) and inflated via inflation line 20. The inflation of the cuff 18 may be manual or may be controlled by the blood pressure monitor 16. As depicted, the sensor 14 is associated with the cuff 18 on an interior (e.g., tissue-contacting) surface 22 such that the sensor 14 is at least partially covered by the cuff 18. In certain embodiments, the sensor 14 is positioned at an approximate mid-point 23 of the tissue-contacting surface, which may assume a curved profile when fully inflated. When the cuff 18 is inflated, pressure is applied to the area of the limb under the cuff 18 and the sensor 14 is pressed against the tissue. As a result of the increased pressure, a blood vessel 24 is constricted corresponding to the area 26 of the limb where the cuff 18 is applied. The constriction of the blood vessel 24 leads to hemodynamic changes that may be monitored by the system 10 for a more accurate noninvasive blood pressure measurement as provided.

Figure 2:
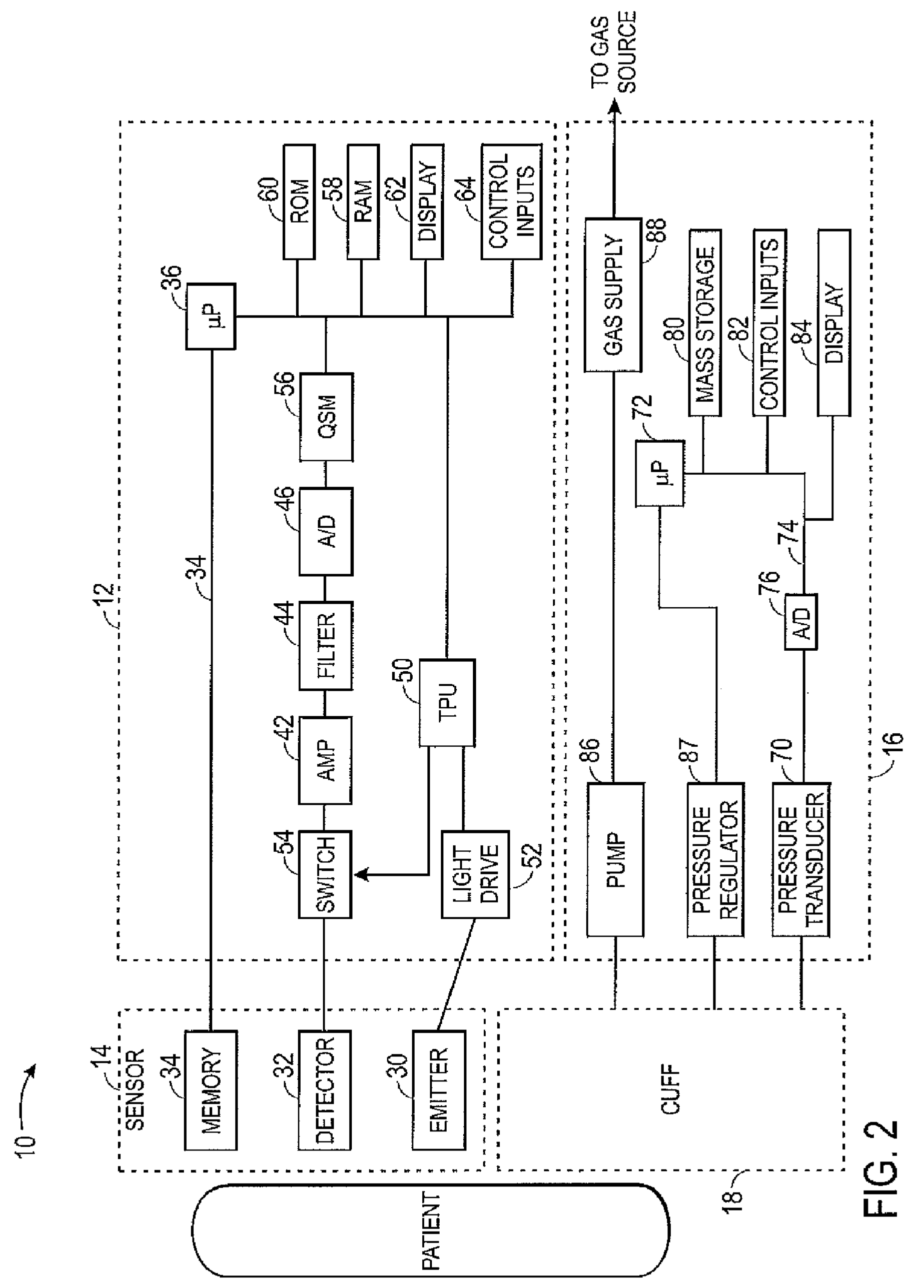
FIG. 2 is a block diagram of the medical monitoring system of FIG. 1, in accordance with an embodiment.

FIG. 2 is a block diagram of the system 10. As noted, the photoplethysmography sensor 14 may be associated with the cuff 18. In one embodiment, the photoplethysmography sensor 14 may be a standard pulse oximetry sensor capable of being coupled to the monitor 12, which may be a pulse oximetry monitor. Examples of pulse oximetry sensors and monitors may be available from Nellcor Puritan Bennett, L.L.C. The photoplethysmography sensor 14 may include an emitter 30 capable of emitting one or more wavelengths of light, e.g., RED and/or infrared (IR) light, into the tissue of a patient, In particular embodiments, as provided herein, the photoplethysmography sensor 14 may emit any wavelength of light within the full bandwidth spectrum, and the detector 32 may be capable of detecting light at various intensities and wavelengths. As used herein, the term "light" may refer to one or more of ultrasound, radio, microwave, millimeter wave, infrared, visible, ultraviolet, gamma ray or X-ray electromagnetic radiation, and may also include modulated light. The emitter 30, for example, may emit red wavelength light between about 600 nanometers (nm) and about 700 nm and/or IR wavelength light between about 800 nm and about 1000 nm. In other embodiments, the emitted light may be less than about 600 nm. The emitter 30 may include a single emitting device, for example, with two light emitting diodes (LEDs), or the emitter 30 may include a plurality of emitting devices with, for example, multiple LED's at various locations. In such embodiments, the data provided by the photoplethysmography sensor 14 may be used to calculate physiological parameters, such as blood oxygen saturation and pulse rate, in addition to tracking the emergence of the plethysmographic waveform by the monitor 14 and/or the blood pressure monitor 16. Use of several emitters 30 or detectors 32 may also be beneficial for measuring blood flow patterns at several places along the arm, In such embodiments, data from the optical components may be used to determine if the center (e.g., mid-point 23) of the cuff 18 is not the desired or most accurate location on the cuff 18 to measure blood flow, which may be the case if the cuff 18 is improperly positioned, the wrong size for the patient, or if maximum pressure is not in the center due to the positioning of cuff 18 and shape of the arm underneath the cuff.

However, in other embodiments, the photoplethysmography sensor 14 may be configured to emit a single wavelength of light at any suitable wavelength that is capable of generating a plethysmographic waveform at the detector 32. In embodiments in which the data generated by the photoplethysmography sensor 14 is not used for direct calculation of physiological parameters, an emitter 30 configured to emit a single wavelength of light may provide sufficient information related to the emergence of a plethysmographic waveform to the monitor 12. In addition, while the monitor 12 may be capable of calculating physiological parameters, such as heart rate and blood oxygen saturation, in certain embodiments, the monitor 12 may be configured to detect the presence or absence of a plethysmographic waveform and may lack additional functionality for determining physiological parameters blood oxygen saturation. In such embodiments, the emitter 30 and its associated emission wavelength may be selected according to performance, manufacturing, and cost considerations. For example, when the vessels of the arm are occluded, the oxygen saturation of the blood may change. With wavelengths other than the isobestic point (approximately 808 nm), arterial and venous saturation levels may affect the pulse amplitudes. For this reason, in certain embodiments it may be advantageous to use an emitter 30 capable of emitting at a wavelength near or about 808 nm for pulse amplitude considerations. At approximately 808 nm, the absorption of oxygenated blood and de-oxygenated blood is about equal.

In operation, light enters the detector 32 after propagating through the tissue of the patient. The detector 32 may convert the light at a given intensity, which may be directly related to the absorbance and/or reflectance of light in the tissue of the patient, into an electrical signal. Each sensor 14 may also include an encoder 34, which may contain information about the sensor 14, such as what type of sensor it is (e.g., a type of sensor, a location where the sensor is to be placed, etc.) and how the sensor 14 is to be driven (e.g., wavelength of light emitted by the emitter 30). This information may allow the monitor 12 to select appropriate algorithms and/or calibration coefficients or to derive a filter for estimating the patient's physiological characteristics. The encoder 34 may, for instance, be a memory on which one or more of the following information may be stored for communication to the monitor 12. In some embodiments, the data or signal from the encoder 34 may be decoded by a detector/decoder in the monitor 12. For example, the sensor 14 may be store calibration information as in the Nellcor™ RCal or DigiCal calibration systems as provided in U.S. Patent Application No. 20090247852, the specification of which is incorporated by reference in its entirety herein for all purposes. In one embodiment, the calibration information may relate to whether the photoplethysmography sensor 14 is capable of providing blood oxygen saturation information based on the configuration of the optical components. For example, a sensor 14 with a single emitter 30 may not be capable of providing data from which blood oxygen saturation may be calculated with a standard pulse oximetry monitor.

The monitor 12 may include a microprocessor 36 coupled to an internal bus 34. The received signal from the photoplethysmography sensor 14 may be passed through an amplifier 42, a low pass or bandpass filter 44, and an analog-to-digital converter 46. Applying a bandpass filter to the signal may distort the pulse while mitigating effects of noise, for instance from cuff inflation and deflation. In embodiments in which the signal from the sensor 14 may be used to detect presence of absence of pulse rather than for calculating physiological parameters, such distortion may allow for improved detection of the plethysmographic waveform. In some embodiments, the bandpass filter may avoid distorting the pulse amplitude if the amplitude is analyzed to track blood pressure or estimate appropriate cuff inflation or deflation rates. A time processing unit (TPU) 50 may provide timing control signals to light drive circuitry 52, which controls when the optical components of the optical sensor (e.g., photoplethysmography sensor 14) is activated, and, if multiple light sources are used, the multiplexed timing for the different light sources. TPU 40 may also control the gating-in of signals from sensor 14 through a switching circuit 54. These signals are sampled at the proper time, depending at least in part upon which of multiple light sources is activated, if multiple light sources are used. The digital data may then be stored in a queued serial module (QSM) 56, for later downloading to RAM 58 or ROM 60 as QSM 56 fills up. In addition, the monitor 12 may include a display 62 and control inputs, such as knobs, switches, keys and keypads, touchscreens, buttons, etc., to provide for operation and configuration of the monitor 12.

Based at least in part upon the received signals corresponding to the light received by optical components of the photoplethysmography sensor 14, microprocessor 36 may determine the emergence or disappearance of the plethysmographic waveform and may also calculate the oxygen saturation and/or heart rate using various algorithms, such as those employed by the Nellcor™ N-600x™ pulse oximetry monitor, which may be used in conjunction with various Nellcor™ pulse oximetry sensors, such as OxiMax™ sensors. In addition, the microprocessor 36 may calculate a heart rate variability using various methods, such as those provided herein. These algorithms may employ certain coefficients, which may be empirically determined, and may correspond to the wavelengths of light used. The algorithms and coefficients may be stored in a ROM 60 or other suitable computer-readable storage medium and accessed and operated according to microprocessor 36 instructions. In one embodiment, the correction coefficients may be provided as a lookup table. In a particular embodiment, stopping or starting events of the plethysmographic waveform signal may be time stamped for correlation with other events. For example, the time at which the plethysmographic waveform signal reemerges may be correlated to the pressure in the cuff 18 at the same recorded time to determine peak systolic pressure. In addition, based on the correlation of certain events with pulse timing, the system 10 may be used to detect irregular pulses. For example, oscillometric pulses may be used as well as optical sensor data to confirm that irregular beat timing is not a false positive due to noise. The system 10 may provide the data on irregular beat timing to a central station, e.g., for patients in hospital or home care settings.

Figure 3:
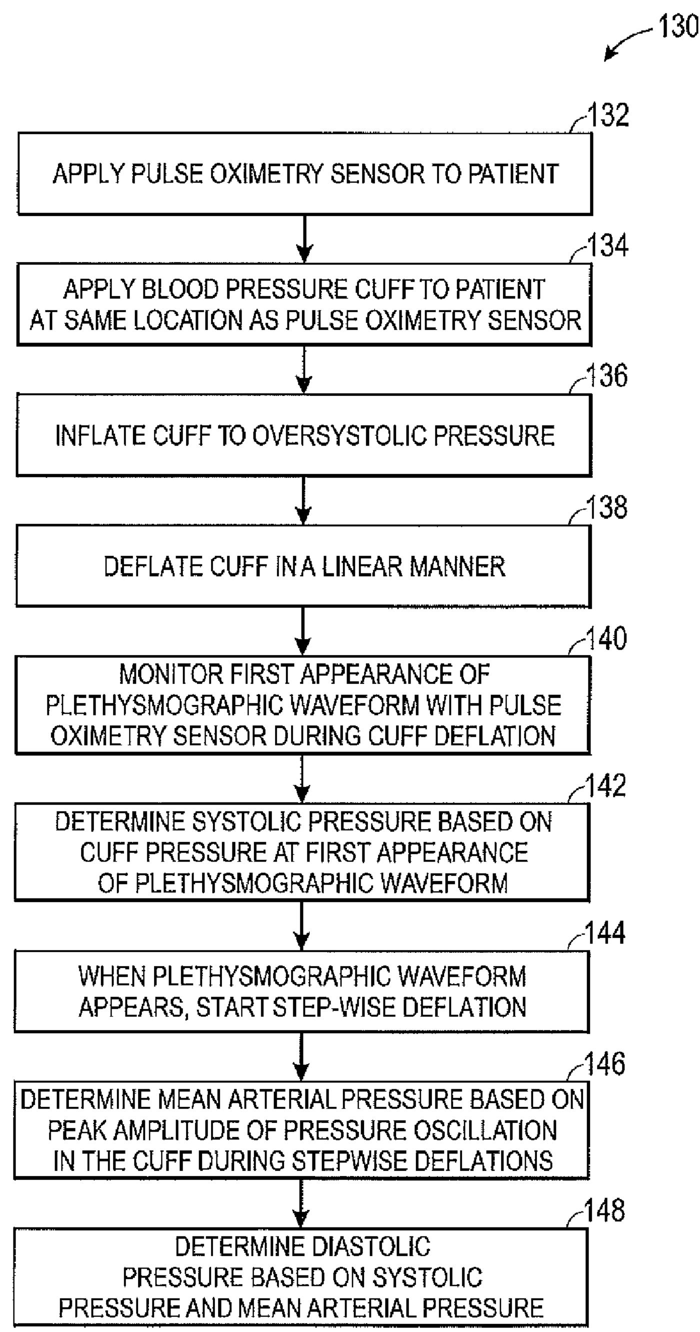
FIG. 3 is a flow diagram of a method on non-invasive blood pressure monitoring in accordance with an embodiment.

The system 10 also includes blood pressure cuff 18 and blood pressure monitor 16. The blood pressure monitor 16 may include a pressure transducer 70 in communication with the cuff 18. In certain embodiments, the pressure transducer 70 may be associated with the cuff 18 or the inflation line 20 and may provide a signal input to the blood pressure monitor 16. The signal from the pressure transducer 70 may be conditioned according to any suitable mechanism, depending on the type of transducer 70 employed. The signal from the pressure transducer 70 may be passed to a processor 72 coupled to an internal bus 74. The blood pressure monitor 16 may also include a mass storage device 80, control inputs 82, and a display 84. The blood pressure monitor 16 may control inflation of the cuff 18 with a pump 86 that is coupled to the inflation line 20, a pressure regulator 87, and a gas supply 88 or a gas source. The inflation of the cuff 18 may be further controlled via inputs from the pressure transducer 70 under control of the microprocessor 76. As provided herein, a pattern of cuff deflation as provided herein may be executed by the processor 76. In addition, input from the monitor 12 indicating that a plethysmographic waveform has been sensed (via sensor 14) during the linear deflation period may trigger certain cuff deflation patterns, The system 10 may be employed for non-invasive blood pressure determination. As noted, data from the photoplethysmography sensor 14 may be used as an input for determining a cuff deflation (or inflation) pattern. In particular, cuff inflation to oversystolic pressure is followed by deflation and concurrent monitoring of pressure oscillations in the cuff during the deflation. FIG. 3 is a process flow diagram illustrating a method 130 for determining heart rate variability in accordance with certain embodiments. The method 130 may be performed as an automated procedure by a system, such as a system 10 that includes monitor 12 and blood pressure monitor 16. In addition, certain steps of the method may be performed by a processor, or a processor-based device that may be part of pulse oximetry monitor 12 and/or blood pressure monitor 16 and that includes instructions for implementing certain steps of the method 130. According to an embodiment, the method 130 begins with coupling the photoplethysmography sensor 14 to a patient at step 132 and applying the blood pressure cuff 18 over the photoplethysmography sensor at step 134. In certain embodiments, the photoplethysmography sensor 14 and the blood pressure cuff 18 may be coupled together and applied as a unitary assembly to the patient.

After the blood pressure cuff 18 is applied to a suitable location (e.g., on a patient's limb), the cuff 18 is inflated to a predetermined pressure that is above systolic pressure for a typical patient at step 136. In one embodiment, the oversystolic pressure may be determined, rather than using a preset pressure, by using the sensor 14 to determine the inflation pressure at which the plethysmographic waveform disappears during a cuff inflation procedure. Determining the oversystolic pressure by monitoring a disappearance or absence of optical pulse detection may be more comfortable for the patient and may provide faster measurements relative to inflating the cuff to a pre-programmed value, which may be set to above systolic for 95% of the population. This may be particularly advantageous in clinical settings in which repeated measurements are taken, such as in long term NIBP monitoring as compared with a single spot cheek.

After reaching the oversystolic pressure, the cuff begins its deflation pattern with a substantially continuous linear period at step 138. During the linear deflation, the cuff pressure may decrease at a specific rate (mmHg/second). The linear deflation proceeds until the photoplethysmography sensor detects a valid pulse in the form of a plethysmographic waveform at step 140. Based on the signal generated by the detector 32, the monitor 12 may determine if a valid pulse has started using any suitable pulse quality and/or identification assessment, such as those provided in U.S. Pat. Nos. 7,534,212, 7,474,907, 7,039,538, and 6,035,223, the specifications of which are incorporated by reference in their entirety herein for all purposes. The pulse qualification may include an assessment of a degree of arrhythmia, pulse amplitude variations, individual pulse quality, or pulse periods. If the assessment indicates that a valid pulse has been detected, the emergence of the detected pulse is correlated to the pressure in the cuff at the time of emergence to determine the systolic pressure at step 142.

Reemergence of the pulse as detected by the first appearance of the plethysmographic waveform also triggers a switch from linear deflation to stepwise deflation at step 144. The cuff pressure is then reduced in predetermined decrements, and pressure fluctuations or oscillations in the cuff 18 are monitored, e.g., via the pressure transducer 70 associated with the cuff. The resultant arterial pulse signals typically consist of a DC voltage with a small superimposed variational component caused by arterial blood pressure pulsations (i.e., oscillations). The oscillation amplitudes measured from the cuff 18 may range from a fraction of a mmHg to as much as 8 mmHg. The peak amplitude of the oscillations during the stepwise deflation of the cuff 18 may be used to determine the mean arterial pressure at step 146, which in combination with the systolic pressure may be used to determine the diastolic pressure at step 148.

After determining the blood pressure, the system 10 may provide any suitable indication or display related to the blood pressure measurement (e.g., systolic and diastolic pressure measurements or mean arterial pressure), such as a graphical, visual, or audio representation of the blood pressure. An indication may include one or more numeric values that are displayed on the monitor 18. In addition, the blood pressure may be stored for later review or may be provided to a centralized medical monitoring system, such as the Nellcor™ Oxinet™ III central station and paging system. In another embodiment, the blood pressure is calculated by an OEM module and communicated, for instance through a serial port, to a multi-parameter monitor.

Figure 4:
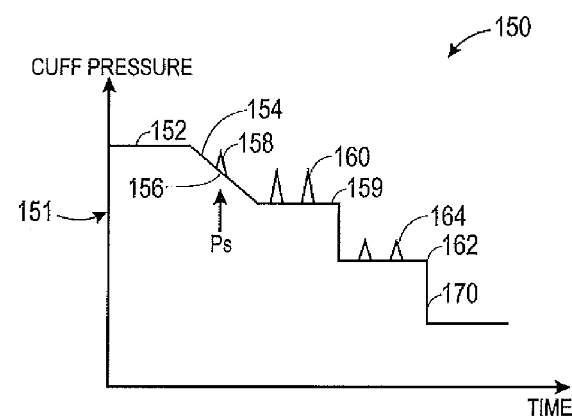
FIG. 4 is an example of a graph of cuff pressure during a cuff deflation pattern in accordance with an embodiment.

FIG. 4 is an example of a graph 150 of cuff pressure during blood pressure monitoring by the system 10. In the depicted example, relative cuff pressure, shown on the y-axis 151, varies over the monitoring period. When the cuff 18 is inflated to an oversystolic pressure 152, blood flow is reduced in the area of the tissue proximate to the cuff 18, which results in the cessation of detected pulse by the photoplethysmography sensor 14. The cuff 18 is deflated in a linear deflation period 154 while the pressure in the cuff is actively monitored via the blood pressure monitor 18. The photoplethysmography sensor 14 is engaged and actively monitoring the tissue (i.e., the emitter 30 is directing light into the tissue that is detected by the detector 32) for the reemergence of a plethysmographic waveform. When the cuff 18 is deflated to the systolic pressure point 156, blood flow resumes and the reemergence 156 of the plethysmographic waveform is detected by the photoplethysmography sensor 14. In certain embodiments, the systolic pressure point 156 may also be marked by an oscillation peak 158 that is capable of being detected by the cuff pressure transducer 70. However, during the linear deflation period 154, this oscillation peak 158 may be obscured by noise. Accordingly, the photoplethysmography sensor 14 may provide a more accurate determination of the systolic pressure relative to the oscillometric method alone.

Once the plethysmographic waveform is detected during the linear deflation period, the monitor 16 may trigger a stepwise deflation pattern in the cuff 18. While stepwise deflation is typically associated with a reduction of noise in the detected oscillations, stepwise deflation may introduce quantization errors to the detection of the plethysmographic waveform. Accordingly, as provided, stepwise deflation of the cuff 18 may commence after determination of the systolic pressure 156. As the cuff pressure drops to lower levels, the peak amplitudes will normally increase from a lower level, e.g., peak 158, to a relative maximum 160 at level 159. The peak amplitudes 164 at continued decrements, e.g., level 162, after detection of the maximum 160 will continue to decrease. These amplitudes form an oscillometric envelope for the patient. The lowest cuff pressure at which the oscillations have a maximum value has been found to be representative of the mean arterial pressure (MAP) of the patient. Systolic and diastolic pressures can be derived either as predetermined fractions of the oscillation size at MAP, or by more sophisticated methods of direct processing of the oscillation complexes. After detection of the relative maximum 160, the cuff 18 may be undergo rapid deflation 170 and subsequent removal.

In one embodiment, the system 10 may employ oscillation pulse amplitude matching at each pressure level to discriminate good oscillations from artifacts. In particular, pairs of oscillation pulses are compared at each pressure level to determine if they are similar in amplitude and similar in other attributes, such as shape, area under the oscillation curve, and/or slope. If the oscillation pulses compare within predetermined limits, the average pulse amplitude and cuff pressure at each level are stored, and the cuff 18 is deflated to the next pressure level for another oscillation measurement. However, if the oscillation pulses do not compare favorably, the monitor 16 may not provide instructions to deflate the cuff 18 further, but instead waits for a good oscillation pulse amplitude match. In one embodiment, this deflation pattern may continue until a relative pulse amplitude maximum is detected that allows the mean arterial pressure to be determined.

Figure 5:
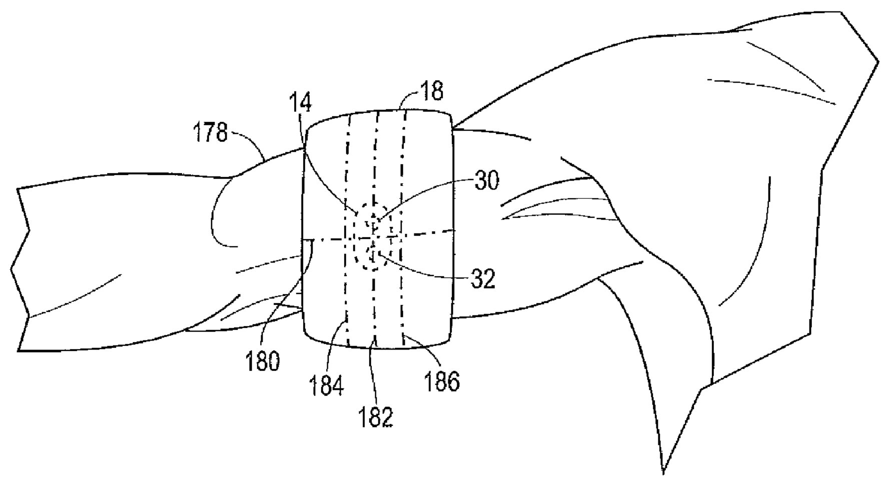
FIG. 5 is a perspective view of a blood pressure cuff and a photoplethysmography sensor applied to a patient in accordance with an embodiment.

As provided herein, the cuff 18 may employ a deflation pattern that uses input from the photoplethysmography sensor 14 to trigger commencement of stepwise deflation. Accordingly, the photoplethysmography sensor 14 is applied to the patient in an area proximate the cuff 18 such that the photoplethysmography sensor 14 is capable of detecting reemergence of the plethysmographic waveform as the cuff 18 is deflated to the systolic pressure and blood flow in the area around the cuff 18 resumes. In certain embodiments, the photoplethysmography sensor 14 is applied to the patient under the cuff 18, as shown in perspective view FIG. 5, such that the photoplethysmography sensor 14 is in direct contact with the patient's tissue 178. In certain embodiments, the position of the photoplethysmography sensor 14 is at or near the point on the cuff 18 at which the maximum applied pressure to the tissue 178. For cuffs 18 that have a generally donut shape that encircles the limb, the point of maximum applied pressure may correspond to the mid point of the curve along the tissue-contacting surface of the cuff (see mid-point 23 of FIG. 1). It is contemplated that monitoring the appearance of the plethysmographic waveform at the point of highest applied pressure to the tissue may result in a more accurate determination of the systolic pressure. Further, in such embodiments, the sensor 14 may be positioned away from the edges of the cuff, as the pressure at the edges may be subject to greater variation, which in turn may introduce inaccuracies in the determination of systolic pressure. Depending on the particular geometry of the cuff 18, the cuff 18 may have a longer circumferential dimension 182 and a shorter dimension along the axis 180. In certain embodiments, the photoplethysmography sensor 14 may be positioned at an approximate midpoint of the cuff's dimension along the axis 180. In other embodiments, the photoplethysmography sensor may be positioned within the approximate middle third of the axis 180, between circumferential lines 184 and 186. The axis 180 may be positioned at any point along the circumference of the cuff 18.

Figure 6:
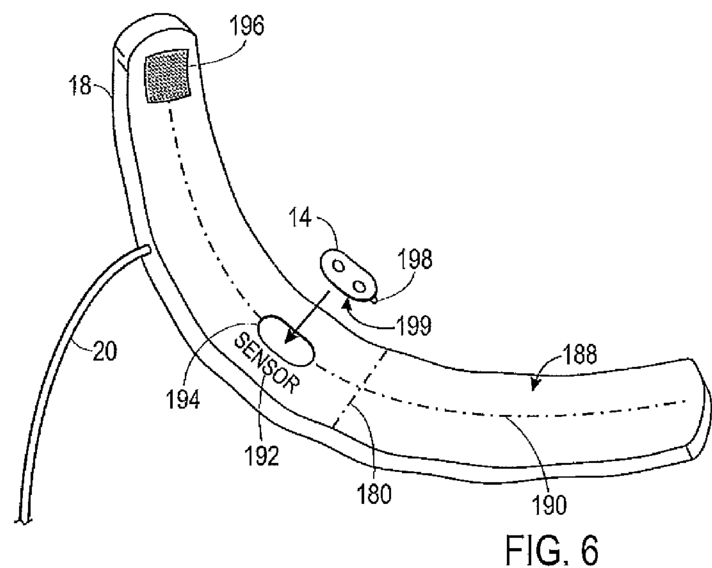
FIG. 6 is a perspective view of a blood pressure cuff with alignment indicators and a photoplethysmography sensor in accordance with an embodiment.
Figure 7:
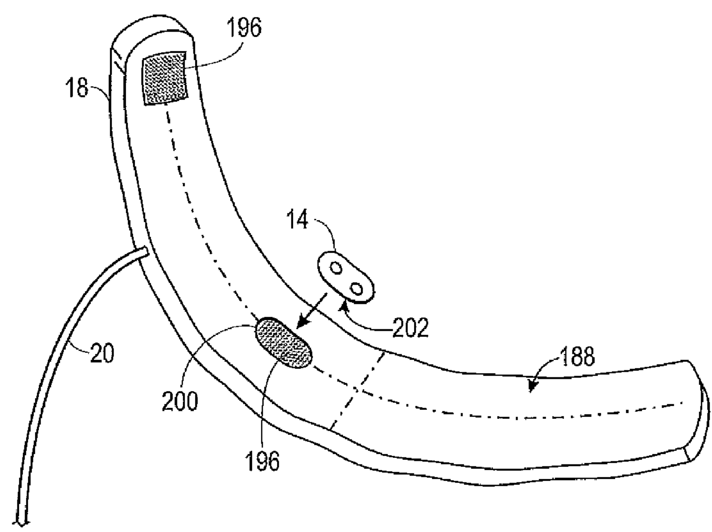
FIG. 7 is a perspective view of a blood pressure cuff with a sensor attachment feature and a photoplethysmography sensor in accordance with an embodiment.

FIG. 6 is a perspective view of an implementation of the cuff 18 that includes various alignment indicators or positioning features to facilitate attachment of the photoplethysmography sensor 14 to a tissue-contacting surface 188 of the cuff 18. For example, the alignment indicators may include an alignment line 190, a text indicator 192, or a box 194 that substantially corresponds to the shape of the sensor 14, In certain embodiments, the sensor 14 may include an adhesive or other mechanism for attachment of a surface 199 to the cuff 18. In certain embodiments, the adhesive may be covered during storage by a protective sheet that may be pulled off via tab 198. It is also envisioned that the photoplethysmography sensor 14 and the cuff 18 may be provided as a kit. In such embodiments, the photoplethysmography sensor 14 may be a standard sensor or may be a sensor with certain features, e.g. adhesive disposed on the surface 199, that facilitate secure attachment to the cuff 18. Further, while the sensor 14 is shown with the optical components aligned along the longest dimension of the cuff 18, in other embodiments the sensor 14 may be positioned in any suitable orientation relative to the cuff 18. For example, the optical components of the sensor 14 may be arranged relative to the cuff 18 in any configuration that permits monitoring of plethysmographic signals. In one embodiment, the emitter 30 may be coupled to a plurality of detectors 32, for example that are arranged in a substantially axial configuration apart from the emitter 30 and at a plurality of separation distances. The active detector 32 may be selected (for example, by the monitor 12) for a desired separation distance from the emitter 30. In addition, multiple emitters 30 may be used to achieve a desired separation distance from the detector(s) 32. Longer separation distances may be associated with deeper tissue penetration, which in particular embodiments may be associated with reduced noise. In one embodiment, a reference emitter 30 and detector 32 may be positioned away from the center of the cuff 18 for comparison with optical components that are placed closer to the cuff's mid-point 23. The reference emitter 30 and detector 32 may provide information that allows the monitor 12 to assess if the cuff 18 and associated sensor 14 are properly sized and positioned. In other embodiments, the reference emitter 30 and detector 32 may be used to confirm the detection of the plethysmographic waveform.

In particular embodiments, the cuff 18 may be available in different sizes to conform to different arm circumferences. In other embodiments, the cuff 18 may be an adjustable or universal cuff that is capable of conforming to a range of circumferences. For example, the cuff 18 may include a hook and loop style adjustment feature 196 that is configured to mate with a corresponding feature on the cuff 18. In certain embodiments, the sensor 14 may also include a hook and loop attachment feature 202 that is configured to mate with a corresponding feature 200 on the surface of the cuff 18. In such embodiments, it is envisioned that, if the cuff adjustment feature 196 is a hook feature (e.g., for mating with a corresponding loop region), the attachment feature 202 on the sensor 14 may be selected to be prevented from being inadvertently positioned on the adjustment feature 196. That is, the attachment feature 202 may a hook region that cannot be mated with a hook-type adjustment feature 196. In addition, the indicators or attachment points on the cuff 18 may be positioned in an area of the tissue-contacting surface 188 of the cuff 18 that is not configured to be pulled out of contact with the tissue when the cuff 18 is adjusted to its smallest size.

Figure 8:
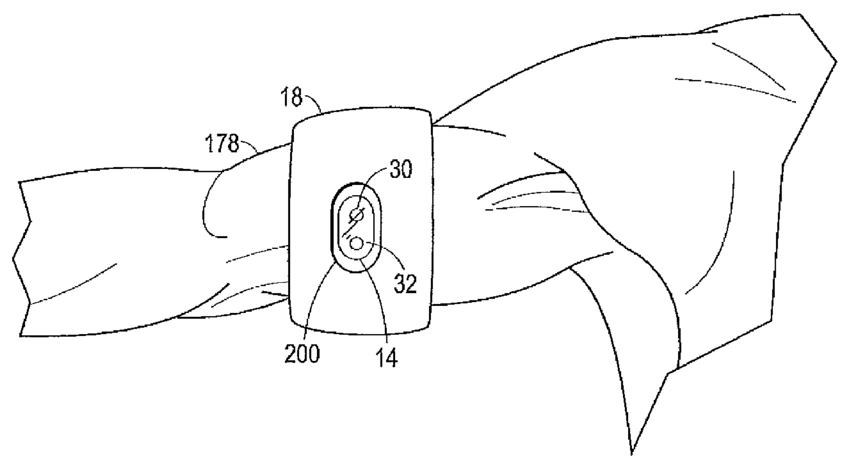
FIG. 8 is a perspective view of a blood pressure cuff with a transparent region and a photoplethysmography sensor applied to a patient in accordance with an embodiment.

In other embodiments, the cuff 18 may be formed at least in part from transparent materials so that the position of the photoplethysmography sensor 14 relative to the cuff 18 may be assessed by an observer. Such an embodiment may be advantageous in implementations in which a standard photoplethysmography sensor is applied to the skin via an adhesive or other securing mechanism, and the cuff 18 is then positioned over the photoplethysmography sensor 18. As shown in FIG. 8, the cuff 18 may include a transparent region 200. When the cuff 18 is positioned over the photoplethysmography sensor 14, the transparent region 200 may be aligned with the sensor 14 to facilitate proper positioning of the cuff 18 relative to the sensor 14. The transparent region 200 provides a viewing window that allows confirmation that the photoplethysmography sensor 14 is correctly positioned throughout the monitoring process. It is also envisioned that the pressure of the cuff 18 may provide securing force to the sensor 14.

As noted, sensors 14 may be provided that include certain features that facilitate use with a cuff 18. The sensors 14 may include conformable sensor bodies and cables that may improve contact with the patient's tissue and may fit easily under the cuff 18. In one embodiment, the electrical connections of the sensor 14 may be printed on a flexible circuit. Further, the cuff 18 may employ a connector that combines inflation line 20 and electrical connections for the optical components in a single assembly. For example, a DB9-style connector may be arranged so that an air hose may be incorporated into the coaxial cable slot.

Figure 9:
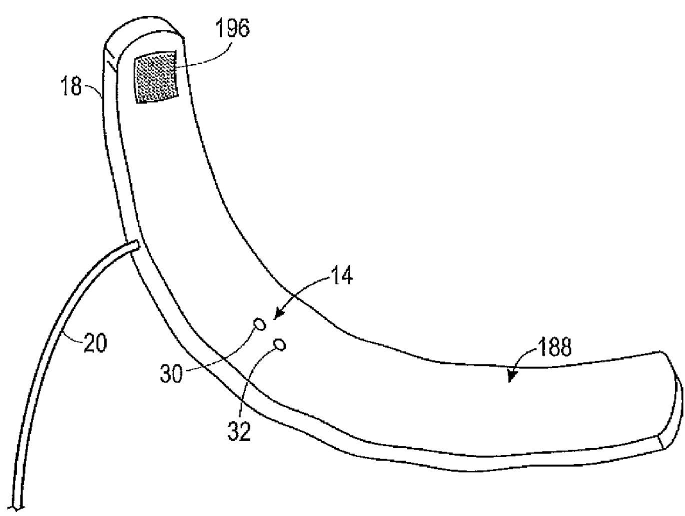
FIG. 9 is a perspective view of a blood pressure cuff with an integral photoplethysmography sensor in accordance with an embodiment.

In addition, providing the photoplethysmography sensor 14 and the cuff 18 as separate components may provide certain advantages for the clinician. For example, the photoplethysmography sensors 14 configured to be used with the cuff 18 may be generally conformable bandage-type sensors that designed as single-use products, while the cuffs 18 may be reusable. Accordingly, a clinician may separate a used sensor 14 from the cuff 18 and apply a new sensor 14 for each use. Alternatively, as shown in FIG. 9, the emitter 30 and detector 32 of the sensor 14 may be sewn into the tissue-contacting surface 188 or otherwise formed as a unitary assembly with the cuff 18. Providing the sensor 14 as a non-removable component of the cuff 18 may prevent user error in positioning the sensor 14 relative to the tissue-contacting surface of the cuff.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims,

What is claimed is:

1. A medical device comprising:

a sensor configured to acquire photoplethysmography data and generate a signal relating to the photoplethysmography data, wherein the sensor comprises a flexible, bandage-type sensor body; and an inflatable blood pressure cuff configured to be coupled to a pressure transducer, wherein the sensor is removably disposed on a tissue-contacting surface of the inflatable blood pressure cuff.

2. The medical device of claim 1, wherein the sensor comprises only one light emitter.

3. The medical device of claim 2, wherein the light emitter is configured to emit light with a wavelength that is in a range of about 600 nm to about 1,000 nm.

4. The medical device of claim 2, wherein the light emitter is configured to emit light at a wavelength where the optical absorption from oxygenated and de-oxygenated hemoglobin is substantially equal.

5. The medical device of claim 1, wherein the sensor comprises at least one light emitter and at least one light detector, and wherein the light emitter and the light detector are attached to a material that forms a surface of the inflatable blood pressure cuff

6. The medical device of claim 1, wherein the sensor is reversibly affixed to the inflatable blood pressure cuff.

7. The medical device of claim 1, wherein the tissue-contacting surface of the blood pressure cuff comprises one or more alignment indicators configured to align the sensor on the tissue-contacting surface.

8. The medical device of claim 7, wherein the one or more alignment indicators comprise an attachment element configured to fix the sensor to the tissue-contacting surface.

9. The medical device of claim 1, wherein the inflatable cuff comprises a window configured so that the sensor may be viewed by an observer when the medical device is applied to the patient.

10. The medical device of claim 1, wherein the sensor is not disposed on the edges of the inflatable blood pressure cuff.

11. The medical device of claim 1, wherein the sensor is disposed on a portion of the tissue-contacting surface of the inflatable balloon cuff that applies a largest force to a tissue when applied to a patient.

12. A medical device comprising:

an inflatable blood pressure cuff configured to be coupled to a pressure transducer and comprising an alignment indicator disposed on an interior surface of the blood pressure cuff, wherein the alignment indicator is positioned to align a photoplethysmography sensor on a surface of the inflatable blood pressure cuff such that the photoplethysmography sensor is configured to be between the tissue and the inflatable blood pressure cuff when the medical device is applied to a patient.

13. The medical device of claim 12, wherein the alignment indicator comprises an alignment instruction.

14. The medical device of claim 12, wherein the alignment indicator comprises a hook and loop fastener.

15. The medical device of claim 12, wherein the alignment indicator comprises a window or transparent region that allows an observer to view the sensor through the inflatable balloon cuff, and wherein a first surface of the sensor is disposed on the surface of the inflatable blood pressure cuff and a second surface of the sensor is configured to be disposed on the tissue.

16. A method comprising:

positioning a photoplethysmography sensor on a tissue contacting surface of a blood pressure cuff;

applying the inflatable blood pressure cuff and the photoplethysmography sensor to a patient; and removing the photoplethysmography sensor from the tissue contacting surface of the blood pressure cuff.

17. The method of claim 16, comprising positioning the photoplethysmography sensor at a position that correlates to a greatest applied pressure of the inflatable blood pressure cuff.

18. The method of claim 16, comprising positioning the photoplethysmography sensor at a position that correlates to a point that corresponds to a midpoint of a shortest dimension of the blood pressure cuff.

19. The method of claim 16, comprising positioning the photoplethysmography sensor at a position that correlates to an alignment indicator on the blood pressure cuff.

* * * * *